United States Patent
Wapner et al.

(10) Patent No.: US 6,982,787 B1
(45) Date of Patent: Jan. 3, 2006

(54) MODIFICATION OF THE DEGREE OF LIQUID CONTACT WITH A SOLID BY CONTROL OF SURFACE AND MICRO-CHANNEL CAPILLARY GEOMETRY

(75) Inventors: Phillip G. Wapner, Palmdale, CA (US); Wesley P. Hoffman, Palmdale, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 340 days.

(21) Appl. No.: 10/340,381

(22) Filed: Jan. 2, 2003

Related U.S. Application Data

(60) Provisional application No. 60/344,063, filed on Jan. 2, 2002.

(51) Int. Cl.
*G01C 1/00* (2006.01)
(52) U.S. Cl. .................................... 356/138; 73/53.01
(58) Field of Classification Search .............. 356/138; 73/53.01, 53.06, 53.07, 54.12
See application file for complete search history.

(56) References Cited

U.S. PATENT DOCUMENTS

| | | | |
|---|---|---|---|
| 4,233,029 A * | 11/1980 | Columbus ................... | 436/174 |
| 4,688,938 A | 8/1987 | Demoulin et al. | |
| 5,080,484 A | 1/1992 | Schneider et al. | |
| 5,137,352 A | 8/1992 | Blitshteyn et al. | |
| 5,143,744 A | 9/1992 | Barth et al. | |
| 5,526,546 A | 6/1996 | Kamen | |
| 5,708,506 A | 1/1998 | Birang | |
| 5,815,256 A | 9/1998 | Fukunaga | |
| 5,838,445 A | 11/1998 | Sandhu et al. | |
| 5,861,946 A | 1/1999 | Hudson et al. | |
| 6,221,955 B1 | 4/2001 | Mequanint et al. | |
| 6,222,184 B1 | 4/2001 | Kinnunen | |
| 6,232,521 B1 * | 5/2001 | Bewick-Sonntag et al. . | 604/378 |
| 6,280,883 B1 | 8/2001 | Lamanna et al. | |
| 6,288,157 B1 | 9/2001 | Jariwala et al. | |
| 6,291,022 B1 | 9/2001 | Hong et al. | |
| 6,299,981 B1 | 10/2001 | Azzopardi et al. | |
| 6,312,808 B1 | 11/2001 | Veerasamy et al. | |
| 6,340,192 B2 | 1/2002 | Pike et al. | |
| 6,353,051 B1 | 3/2002 | Huang | |
| 6,368,664 B1 | 4/2002 | Veerasamy et al. | |
| 6,370,947 B1 | 4/2002 | Casati et al. | |
| 6,531,206 B2 * | 3/2003 | Johnston et al. ............ | 428/172 |
| 6,581,438 B1 * | 6/2003 | Hall et al. .................. | 73/53.01 |

\* cited by examiner

*Primary Examiner*—Layla G. Lauchman
(74) *Attorney, Agent, or Firm*—AFMCLO/JAZ; Charles E. Bricker

(57) ABSTRACT

A method of modifying the apparent wettability (the area contacted by a liquid) of solids with liquids by controlling the surface geometry or the capillary geometry. This modification is possible by understanding the geometric relationship between the contact angle and the included angle of surface features. This same geometric relationship can be used to control entrance of a liquid into a capillary and the flow of more than one fluid in distinct streams through a capillary device.

14 Claims, 10 Drawing Sheets

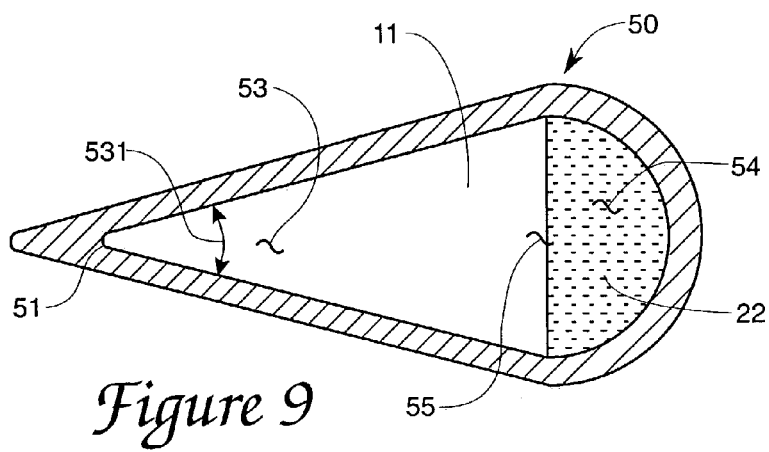
*Figure 9*
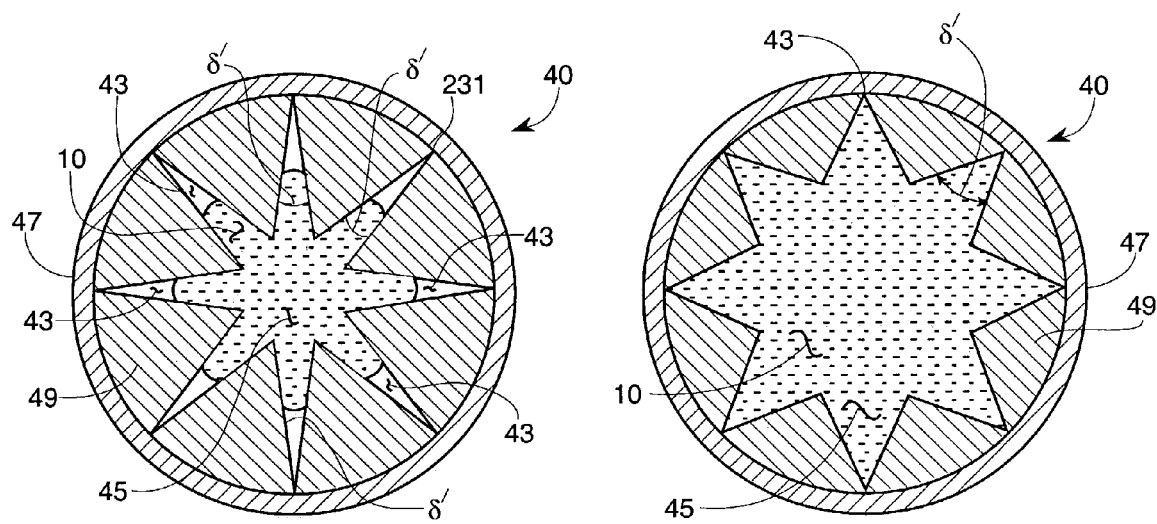
*Figure 8c*   *Figure 8d*

MODIFICATION OF THE DEGREE OF LIQUID CONTACT WITH A SOLID BY CONTROL OF SURFACE AND MICRO-CHANNEL CAPILLARY GEOMETRY

CROSS REFERENCE TO RELATED PATENT DOCUMENT

This application claims priority from U.S. provisional application Ser. No. 60/344,063; filed Jan. 2, 2002.

RIGHTS OF THE GOVERNMENT

The invention described herein may be manufactured and used by or for the Government of the United States for all governmental purposes without the payment of any royalty.

The present document is somewhat related to the commonly assigned, copending and filed of even date herewith patent document "Liquid To Solid Angle Of Contact Measurement," U.S. Pat. No. 6,687,854. The contents of this and all other documents referenced herein are incorporated by reference.

BACKGROUND OF THE INVENTION

The wetting behavior of a liquid on a solid surface is a phenomenon of significant practical importance. The angle of liquid to solid contact on a solid surface is important in diverse areas of science and technology, such as, adhesion, adsorption, lubrication, catalysis, solid-liquid reaction kinetics, heat transfer, electrical conduction, and micro-fluidic devices. This angle of contact, called the contact angle ($\theta$), is one way to measure and assesses the phenomenon of liquid-solid wetting.

The contact angle $\theta$ of a liquid on a surface may be used to define to what extent, if any, a liquid will "wet" or contact a surface. Whenever a liquid contacts a solid surface, several different types of behavior can be exhibited. At one extreme, a drop of liquid contacting a solid surface will spread out until it forms a thin film on the surface. This is called total wetting and in this case the liquid has a contact angle $\theta$ of zero with the surface. At the other extreme, a drop of liquid will sit on the surface with minimal contact. This behavior is termed total non-wetting and the liquid in this case forms a contact angle $\theta$ of 180° with the surface. For situations in between these extremes, a drop will be formed that makes a well-defined contact angle, $\theta$, with the surface. This is called partial wetting.

The standard historical convention applied to the partial wetting behavior is that if the contact angle is less than 90 degrees, the liquid "wets" the surface. If the contact angle is greater than 90 degrees, the liquid "does not wet" the surface and is termed "non-wetting". In the present document, the terms "wet", "wetting", "not wet", and "non-wetting" will be used to refer to this partial wetting behavior and not to the absolute definitions.

The intrinsic contact angle $\theta_i$ is the angle between a static liquid and a smooth planar horizontal surface. This contact angle is only dependent on the material properties of the liquid and the smooth planar horizontal surface. The apparent or observed contact angle $\theta_a$ will differ from the intrinsic contact angle due to contamination, imperfections, and/or roughness. (With the roughness being on a scale that is small compared to the size [diameter] of the drop.) In contrast to both the intrinsic and apparent contact angle, the dynamic contact angle $\theta_d$ is measured on a drop that is changing size or position and not necessarily on a horizontal surface. In this invention the term contact angle $\theta$ will be used as a general term encompassing whichever of these three contact angles that is applicable for the situation.

Because the wettability of liquids on solid surface is important to quantify, there have been many approaches used to measure the contact angle of a liquid on a solid surface. Prior art approaches have included the sessile drop method, the tilting plate method, the Wilhelmy plate, and the capillary rise method. Typically, the wettability of a surface is determined largely by the intrinsic contact angle $\theta_i$ that the liquid makes with the solid surface.

It should be noted that although the contact angle $\theta$, is the most common way to measure and assesses the phenomenon of liquid-solid wetting, it alone does not adequately describe all aspects of solid-liquid interaction in every situation. For example, the measurement of the contact angle alone is not always precise in quantifying the degree of contact between a liquid and a solid surface. That is, the concept of wettability in its most precise definition is based on the contact angle that the liquid makes with the surface at the perimeter of the liquid. It does not deal, for instance, with the area of contact between the liquid and the solid surface.

In some situations it is desirable to be able to alter the wettability of a surface. That is, to be able to increase or decrease the area of the surface in intimate contact with the liquid. In the past, this has only been possible by changing the character of the liquid or of solid in some manner, such as, by employing a liquid additive (for example, a surfactant), applying a surface coating, or changing the surface energy, for example. For some liquid-solid systems it is not desirable to modify either the solid surface or the liquid.

In this invention it will be demonstrated that it is easily possible to modify the degree of liquid-solid contact by altering only the non-planar features on a solid surface or the shape of a capillary. The liquid-solid contact angle in this situation will remain unchanged. Thus, according to the definition of wettability, the wettability has not changed even though a casual observer would describe this transition in liquid-solid contact as changing from apparent wetting to apparent non-wetting behavior (or vice verse). Wetting and non-wetting do not at all convey the same meaning as fully contacting and partially contacting behavior between a liquid and a solid. Thus, although they can be used interchangeably in many situations, the degree of solid-liquid contact is preferable to the degree of wetting when describing the phenomena that this patent addresses.

Previously, knowledge of the relationship between the contact angle and the degree of solid-liquid contact was limited to planar horizontal surfaces and cylindrical capillaries. The relationship between contact angle and the degree of solid-liquid contact on non-planar and non-horizontal surfaces as well as in capillaries with varying axial dimensions, cross-sectional shapes, and axial shapes has not previously been quantified. An understanding of the contact angle $\theta$ acting in concert with localized non-planar surface features or specific capillary geometries, which is one distinctive feature of this invention, may be used to increase or decrease the area of contact between a liquid and a solid surface.

In the prior art, the degree of contact of a liquid with a surface is determined solely by the contact angle $\theta$ that the liquid makes with the solid surface. In the present invention, the degree of contact of a liquid with a surface or a portion of a surface has also been found to be influenced by the included angle $\delta$ between opposing portions of the surface(s) of the material(s). These opposing surfaces can take numerous forms, such as, plates, pits, pores, trenches, capillaries, etc. The applicants have found that there is a transitional included angle $\phi_t$ for both wetting and non-wetting liquids at which wetting behavior and thus the degree of contact between the liquid and the solid surface changes.

This type of surface modification has application in lubrication of sliding surfaces, fuel catalyst interactions, adherence of coatings, heat transfer and any other solid-liquid combination with a desired wettability.

SUMMARY OF THE INVENTION

This invention provides a method of controlling the area of the surface in intimate contact with the liquid (degree of contact) by controlling the surface geometry of the solid. The surface geometry of the solid may comprise a plurality of surface discontinuities, such as pits, pores or trenches, having at least one solid included angle. On the other hand, it may comprise a plurality of capillaries with each capillary having at least one cross-sectional and/or one axial geometry. The cross-sectional and/or one axial geometry may include at least one capillary included angle.

Alternatively, this invention is able to control the entrance of liquids into and the flow of liquids through free-standing capillaries by proper selection of the cross-sectional and/or one axial geometry of the capillary. This control applies to both wetting as well as non-wetting fluids.

The invention may include a capillary device with a capillary path. The capillary path may carry different fluids in separate streams through the same capillary opening. These different fluids may consist of two or more immiscible non-wetting liquids or of one or more non-wetting liquids and a gas. In the case of two liquids, the first liquid has a first contact angle and the second liquid has a second contact angle. The second contact angle is designed to be greater than the first contact angle. The capillary device may include at least one angular portion and at least one open portion. The fluids are kept separate in the capillary by using angular features in the capillary wall that selectively exclude a liquid on the basis of its contact angle.

It is therefore an object of the present invention to control the wettability of a solid, i.e. the area of the solid contacted by a liquid, by controlling the surface geometry of the solid. It is another object of the invention to control the entrance of liquids into capillaries. It is still another object of the invention to provide a capillary device for carrying different fluids in separate streams through the same capillary opening.

These and other objects of the invention will become apparent as the description of the representative embodiments proceeds.

Portions of the present invention are described in the technical journal article "Partial Wetting Phenomenon on Nonplanar Surfaces and in Shaped Microchannels" authored by the present inventors and published in the American Chemical Society journal Langmuir 2002, 18, 1225–1230. Publication of this same article occurred on the world-wide-web on Jan. 12, 2002. The contents of these publications are hereby incorporated by reference herein.

BRIEF DESCRIPTION OF THE DRAWING

The accompanying drawings incorporated in and forming a part of the specification, illustrate several aspects of the present invention and together with the description serve to explain the principles of the invention. To facilitate understanding of the present invention, like elements have been assigned like identifiers:

FIG. 8c shows a capillary cross sectional geometry embodiment with a non-wetting liquid.

FIG. 8d shows a capillary cross sectional geometry embodiment with a non-wetting liquid.

FIG. 9 shows a capillary device cross sectional geometry embodiment.

DETAILED DESCRIPTION OF THE INVENTION

The following term definitions, consistent with their common meaning may help in understanding the disclosed invention.

"Liquid" refers to any substance composed of molecules that when unconstrained may move freely among themselves but do not tend to separate like a gas.

"non-wetting liquid" refers to a liquid that forms a contact angle with a solid that is greater than 90 degrees.

"Solid" refers to a substance having a relative coherence of molecules and/or particles in a persistent form. Not a gas or liquid.

"Surface geometry" refers to any combination of accessible solid structure. The surface geometry may include any combination of protrusions and/or inclusions such as pillars, columns, pits, voids, capillaries etc.

"Discontinuity" refers to a void, pit, protrusion or other solid irregularity.

"Full contact" or "complete contact" for a non-wetting liquid occurs when the included angle δ or capillary included angle δ' is greater than the transitional included angle $\phi_{tnw}$, such that the non-wetting liquid contacts the vertex of the included angle δ/δ'.

"Partial contact" for a non-wetting liquid occurs when the included angle δ or capillary included angle δ' is less than the transitional included angle $\phi_{tnw}$ such that the non-wetting liquid does not contact the vertex of the angle δ/δ'. E.g. the vertex of the angle formed by the solid is void of liquid.

"Contact angle" θ refers to an angle formed between a liquid and a solid surface.

"Included angle" δ refers to an angle formed between two solid surfaces or by the sides of an inclusion into a solid surface such as a void or a capillary channel.

"Capillary included angle" δ' refers to an angle formed between two solid surfaces of the capillary.

The liquid "radius" r refers to the radius of a liquid droplet. It may also refer to the radius of curvature of a liquid in a void between two solid surfaces, where in the liquid extends between the two surfaces but does not extent into the void vertex.

The subscripts "tnw" and "tw" may be used to differentiate between the non-wetting transitional included angle $\phi_t$ from the wetting transitional included angle $\phi_t$.

"Transition included angle" $\phi_t$ The terms "transitional included angle" and "transitional angle" and "critical angle" and "angle of transition" as used herein may be regarded as making reference to the specific angle at which a liquid sample changes behavior between the apparent wetting characteristics and the apparent non-wetting characteristics or vise versa. It is the angle between two solid sides at which the contacting behavior of a specific liquid changes from fully contacting to partial contacting or from partial contacting to fully contacting.

Figure 1A:
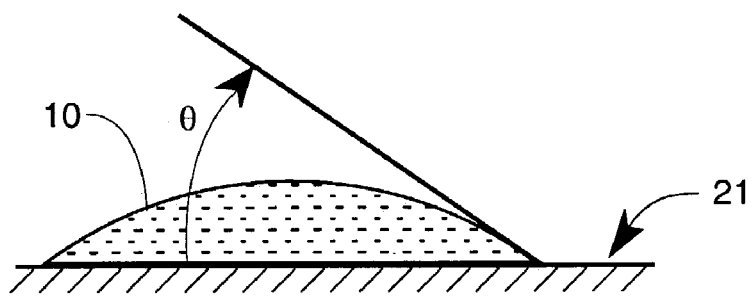
FIG. 1a shows a liquid to solid material contact angle that is greater than zero degrees and less than ninety degrees.
Figure 1B:
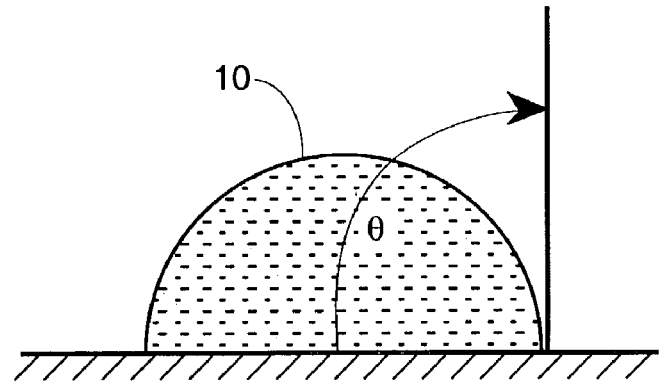
FIG. 1b shows a liquid to solid material contact angle that is equal to ninety degrees.
Figure 1C:
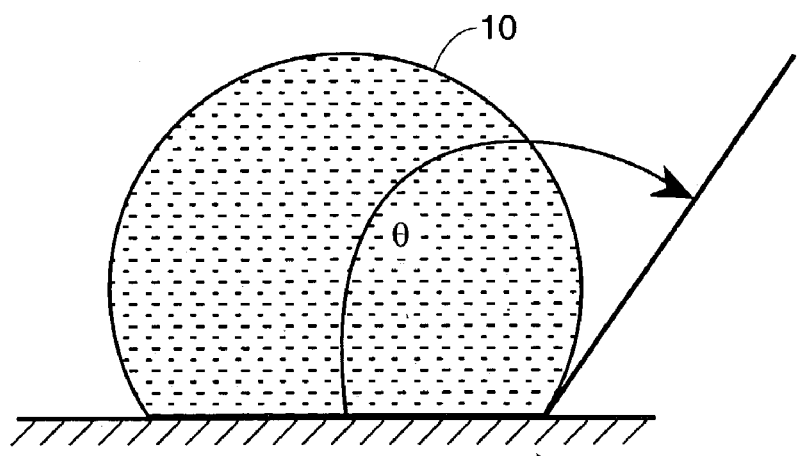
FIG. 1c shows a liquid to solid material contact angle that is greater than ninety degrees but less than one hundred eighty degrees.

FIGS. 1a, 1b, and 1c in the drawings illustrate drops that exhibit different contact angles. FIG. 1a shows a contact angle θ, between 0 degrees and 90 degrees, i.e., of about 45 degrees. FIG. 1b shows a contact angle θ of about 90 degrees. FIG. 1c shows a contact angle θ greater than 90 degrees but less than 180 degrees.

FIGS. 1a–1c show a solid 20 with a solid surface 21 and a liquid 10. As shown in FIGS. 1a–c, the liquid 10 has a contact angle θ, with the solid surface 21. FIG. 1a shows a contact angle θ of between about 0 degrees (00) and about 90°. FIG. 1b shows a contact angle θ of 90°. FIG. 1c shows a contact angle θ greater than about 90° but less than about 180°. For a selected solid 20 and liquid 10, if the contact angle θ is less than about 90°, the liquid 10 will wet or contact the solid surface 21 of the solid 20 as shown in FIG. 1a. If the contact angle θ is about 90°, the liquid 10 may either wet or not wet the solid surface 21 as shown in FIG. 1b. If the contact angle θ is more than about 90°, the liquid 10 will not wet or contact the solid surface 21 as shown in FIG. 1c.

It has been previously assumed in the prior art that if the liquid does not wet the solid surface, that is, the contact angle is greater than 90°, the liquid will not totally contact and/or fill the pits and/or voids in the solid surface. It has also been previously assumed in the prior art that if the liquid does not wet the solid surface, the liquid will not enter a capillary spontaneously. However, it has been determined both theoretically and experimentally that these assumptions do not always reflect reality. The shape of the walls forming pits, voids, and/or capillaries should also be taken into account when determining whether a pit or void in the surface will be filled with the liquid, or if the liquid will enter a particular capillary.

Liquids with Contact Angles θ>90°

Figure 2A:
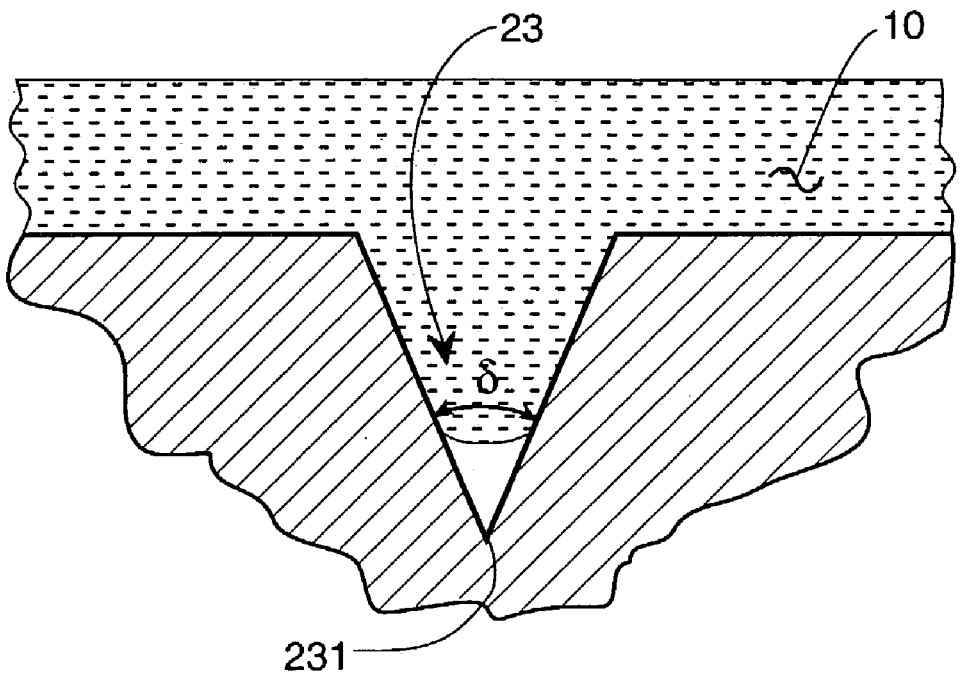
FIG. 2a shows a liquid in a surface void wherein the liquid does not reach the void vertex.
Figure 2B:
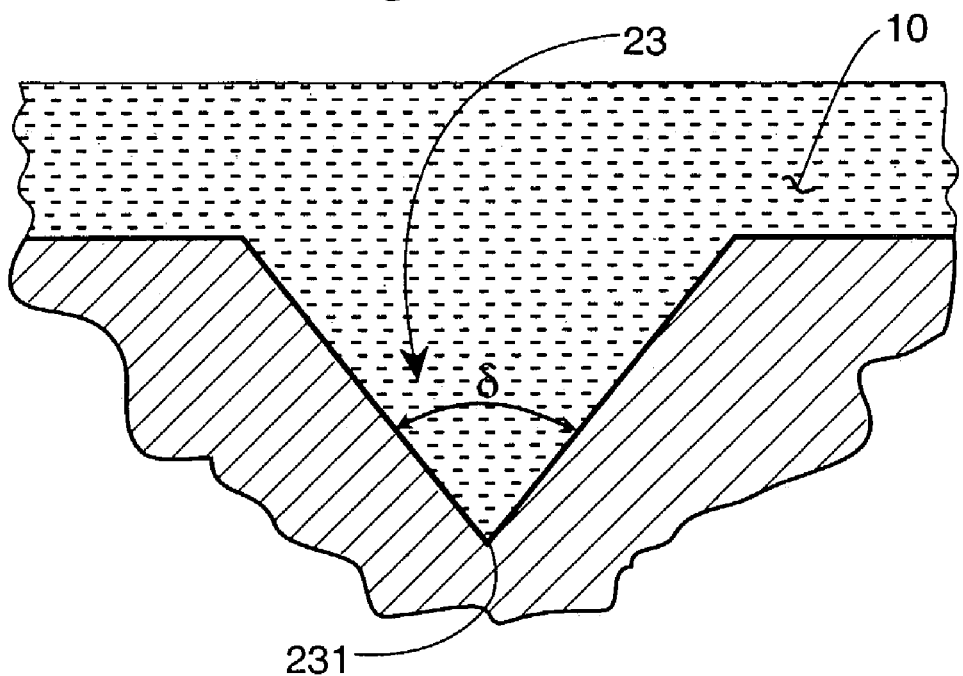
FIG. 2b shows a liquid in surface void 23 wherein the liquid does reach the void vertex.

FIGS. 2a and 2b are an expanded view of simplified surface void 23 having a vertex 231 and an included angle δ. FIG. 2a shows a liquid 10 with a contact angle θ>90° in the surface void 23 wherein the liquid 10 does not reach the void vertex 231. FIG. 2b shows the liquid 10 in the surface void 23 wherein the liquid 10 does reach the void vertex 231. The wettability or degree of contact of the surface void vertex 231 by the liquid 10 may be determined by the contact angle θ, the included angle δ and a transitional included angle $\phi_t$. In order to complete the analysis a transitional included angle $\phi_t$ must be calculated.

Figure 3:
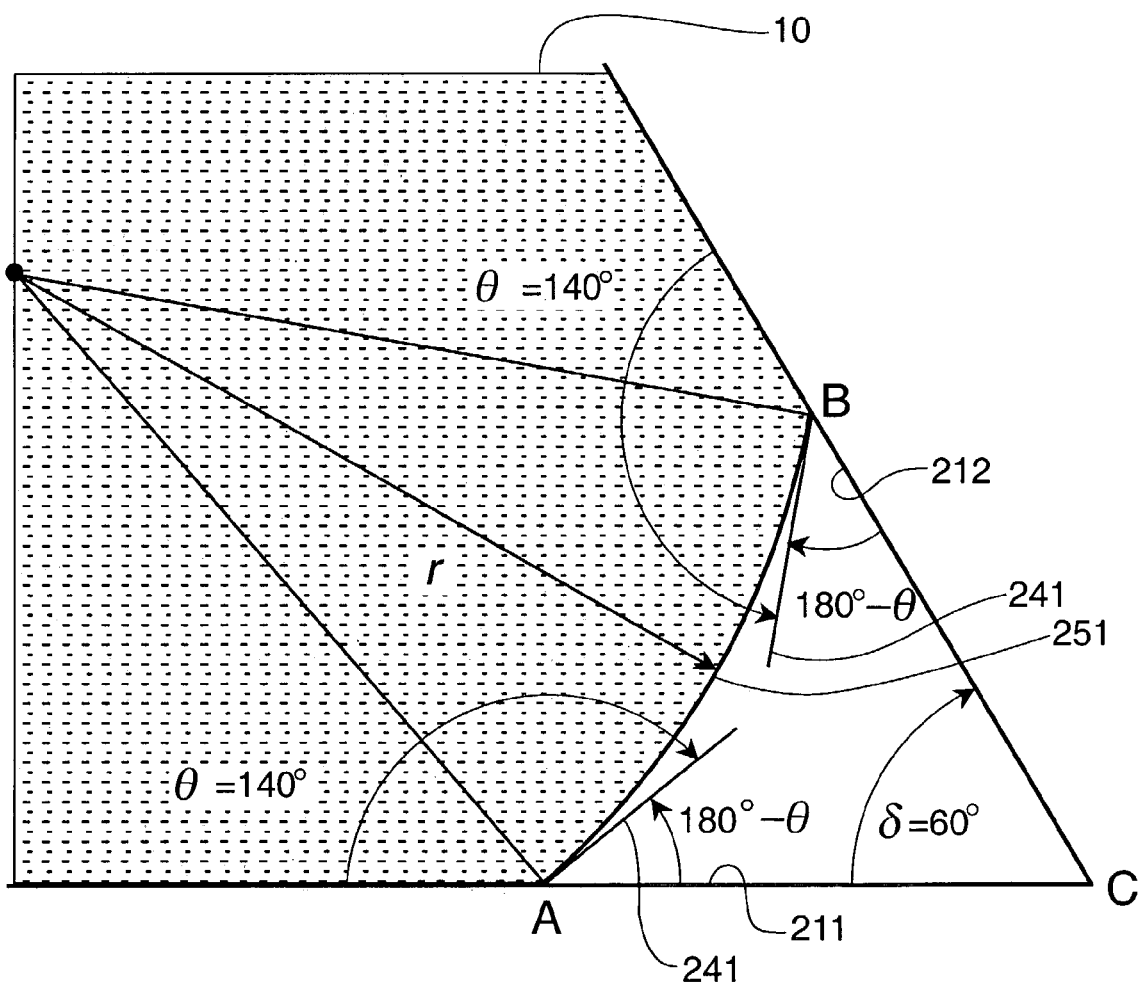
FIG. 3 shows a non-wetting liquid between a first solid surface and a second solid surface and the angular relationships with the contact angle θ.

FIG. 3 shows the non-wetting liquid 10 between a first solid surface 211 and a second solid surface 212. The surfaces could be planar as shown or alternatively a sectional view of another feature such as a cone. This non-wetting liquid has a radius r and an contact angle θ with both solid surfaces of about 140 degrees. The contact angle θ is measured at point B on the second solid surface 212 and at point A on the first solid surface. The vertex of the two surfaces is at point C. FIG. 3 also shows tangents 241 to the liquid surface 251 at the points of contact (points A & B) with the surface. The two plates are shown as intersecting at the vertex although this is not required. The angle formed by ACB, the actual angle formed by the solid, is called the included angle δ. The transitional included angle $\phi_t$ is the included angle δ at which the tangents 241 to the droplet surface 251 originating at points A and B form a straight line. In the example shown in FIG. 3 this would involve rotating the plates about the vertex to create a greater included angle. This transitional included angle $\phi_t$ may be used to differentiate between full contacting (liquid at the vertex C) and partial contacting by the liquid between the two solid surfaces 211 & 212 (no liquid at the vertex C), or in a void. An algebraic analysis of the sides and angles of FIG. 3 provides a means to calculate the transitional included angle $\phi_{tnw}$ for a non-wetting liquid. Thus, $$\phi_{tnw}=2\theta-180° \quad (\theta \geq 90°) \tag{1}$$

Figure 4:
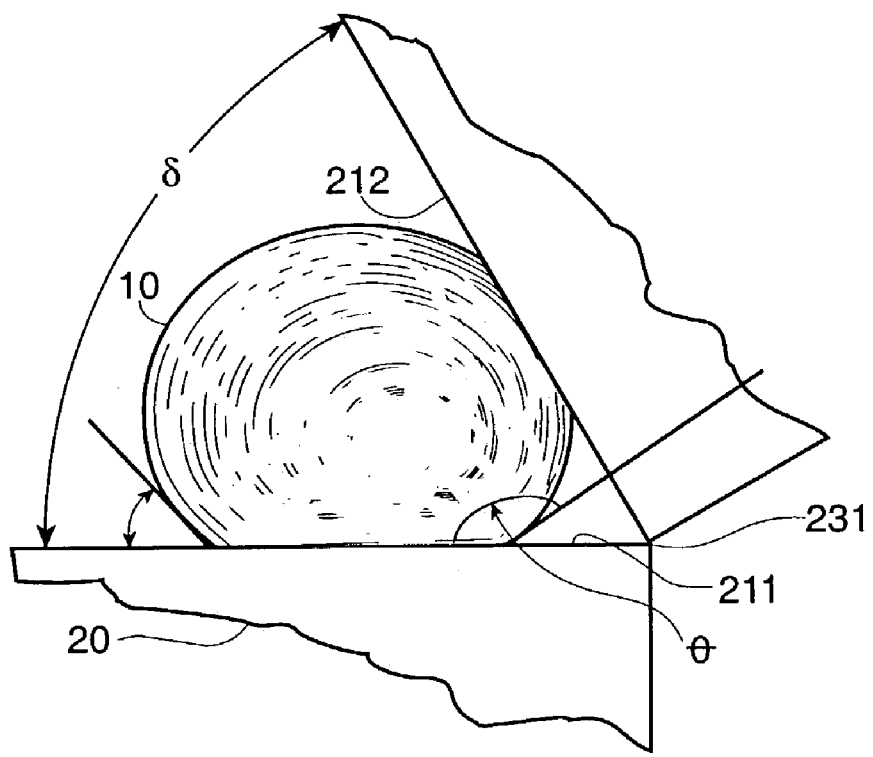
FIG. 4 shows a non-wetting partially contacting liquid (mercury) between two flat plates.
Figure 5:
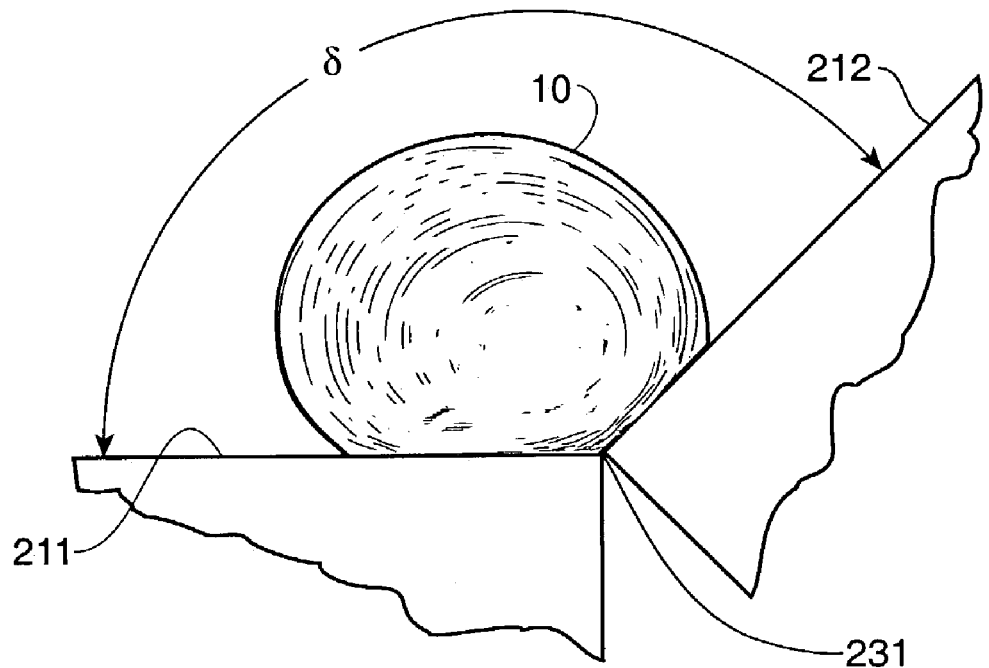
FIG. 5 shows a non-wetting fully contacting liquid (mercury) between two flat plates.

Consequently, for a non-wetting liquid, if the included angle, δ, between the surfaces of pieces of material, between the portions of the surface features of a material, or between opposing walls of a capillary, is greater than 2θ–180° the liquid will "wet" or completely contact the surfaces of the material that encompass the included angle δ. This condition is shown in the drawings of FIG. 5 herein. If the included angle δ is less than this value, the liquid will not "wet" or completely contact the surface and will withdraw from the vertex region 231 of the included angle δ as is shown in the drawing of FIG. 4.

The transitional included angle $\phi_{tnw}$ provides a method of predicting mathematically whether voids and capillaries with included angles may be too small for liquid penetration, or large enough to allow liquid penetration of an otherwise non-wettable material. In a like manner, the transitional included angles $\phi_{tnw}$ or $\phi_{tw}$ provide a method of predicting mathematically the entrance and/or flow of a wetting or non-wetting liquid in a capillary whose walls are not parallel along its entire length. The transitional included angles $\phi_{tnw}$ and $\phi_{tw}$ may be a specific angle or a range of angles.

The relationship between the transitional included angle $\phi_{tnw}$ and the contact angle θ that the non-wetting liquid makes when in contact with the solid surface is given by equation 1. Substituting the value of the contact angle θ for mercury on glass into this equation gives a transitional included angle $\phi_{tnw}$ of 100°, which agrees with experimental results.

By rearranging equation 1, one obtains equation 2:

$$\theta = (\phi_{tnw} + 180°)/2 \quad (\theta \geq 90°) \qquad (2)$$

Equation 2 shows that the contact angle θ of a non-wetting liquid can be easily calculated once the transitional included angle $\phi_t$ for the liquid on the desired surface is known.

It has been discovered that the degree of contact between a liquid 10 and a solid 20 can be influenced by the designed and measured modification of the pits, pores, capillaries, trenches, voids and other liquid access points in a solid surface as well as shaped protrusions on the surface.

In one example shown in FIG. 4, the non-wetting liquid 10 is mercury that has a contact angle θ of about 140° with both the first solid surface 211 on which liquid 10 rests as well as the second solid surface 212 of the solid 20. The first solid surface 211 and the second solid surface 212 can be rotated with respect to a vertex 231 to form any included angle δ between about 0 degrees and about 180 degrees. As can be seen in FIG. 4, and calculated from the above equations, at an included angle δ of about 60°, the liquid 10 is excluded from the vertex 231 intersection of the two solid surfaces 211/212 (i.e., from the interstice region between the two plates). However, if the included angle δ were increased to about 135° as shown in FIG. 5, the non-wetting liquid 10 may fill the vertex 231 intersection of the two solid surfaces 211/212. Clearly there may be a change in the behavior of the liquid 10 as the included angle δ is varied between about 60° and about 135°. This analysis may be applied to surface voids having predicable or otherwise known included angles to calculate the wettability of the voids and thus the solid in general. The complete surface wettability of surface voids may be similarly analyzed based upon the void included angle δ and its relationship to the transitional included angle $\phi_t$, and the contact angle θ.

The above analysis could also be applied to three-dimensional shapes. For example, the behavior of mercury in conical shaped pits could be examined. Cones of PLEXIGLAS® having an included angle δ of 60°, and 82°, and coated with silicon vacuum grease from Dow Corning Corporation could be used. Since the mercury was contacting the vacuum grease, the grease would establish the contact angle θ as being 125°. According to equation 1, a transitional included angle $\phi_t$ of two times 125 degrees minus 180 degrees, should result in a transitional included angle $\phi_t$ of about 70 degrees. From this calculation, it would be expected that when mercury is introduced into the two coated pits, complete contact by the mercury with the vertex would occur in the conical pit having an included conical angle δ of 82 degrees, but not in the conical pit having a conical angle δ of 60 degrees. This was found to be the case. Thus, equation 1 also applies to three-dimensional features. These features may be depressions in the surface or elevations in the surface in the form of pillars, pyramids, etc.

Contact Angle on Non-Planar Surfaces

As previously shown in FIGS. 2a & 2b, the wettability of the solid contacted by a non-wetting liquid may be controlled by controlling the surface geometry of the solid. The surface geometry of the solid may include voids, pits, and protrusions that have included angles δ greater than the transitional included angle $\phi_t$ to increase the area of contact between the liquid and the surface of the solid. Alternatively, a void included angle δ less than transitional included angle $\phi_t$ may be used to decrease the area of contact between the liquid and the surface of the solid surface.

Figure 6:
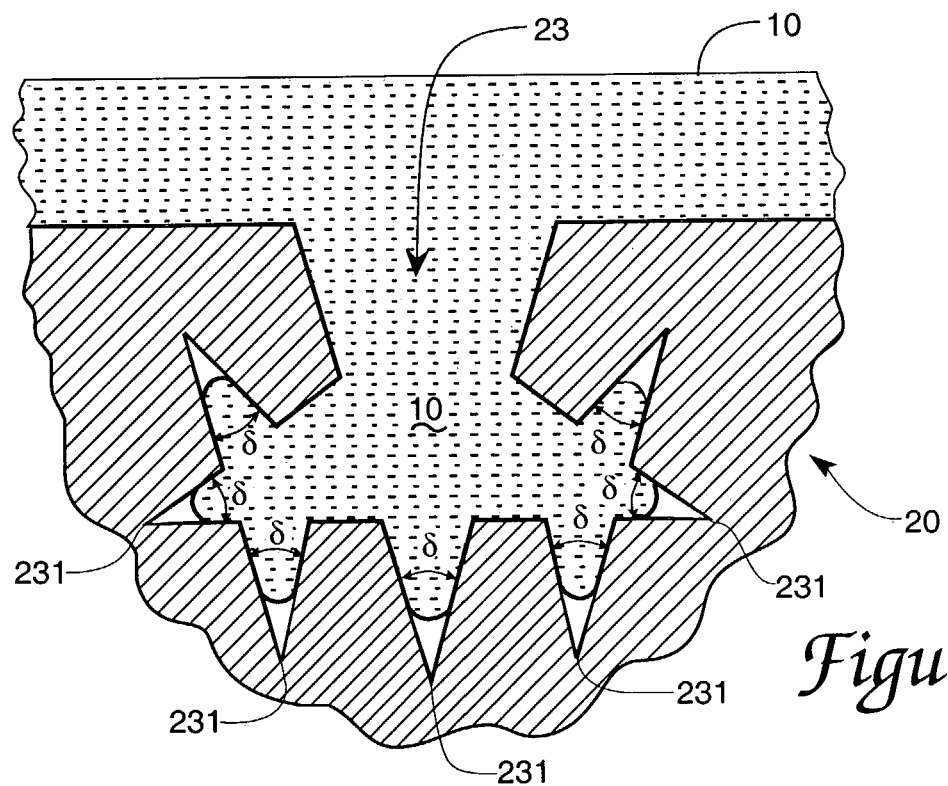
FIG. 6 shows a solid with a void having about 7 void included angles δ wherein the non-wetting liquid does not reach the void vertices.

In some embodiments, the solid surface geometry may comprise a plurality of surface discontinuities. These surface discontinuities (voids etc.) may have the same or different dimensions with one or more void included angles δ such as shown in FIG. 6. FIG. 6 shows a solid 20 with a void 23 having about 7 void included angles δ, which may be the same or different dimensions. In FIG. 6, the included angles δ are less than the transitional included angle $\phi_t$ and complete contact between the non-wetting liquid 10 and the void vertex 231 does not occur.

Figure 7:
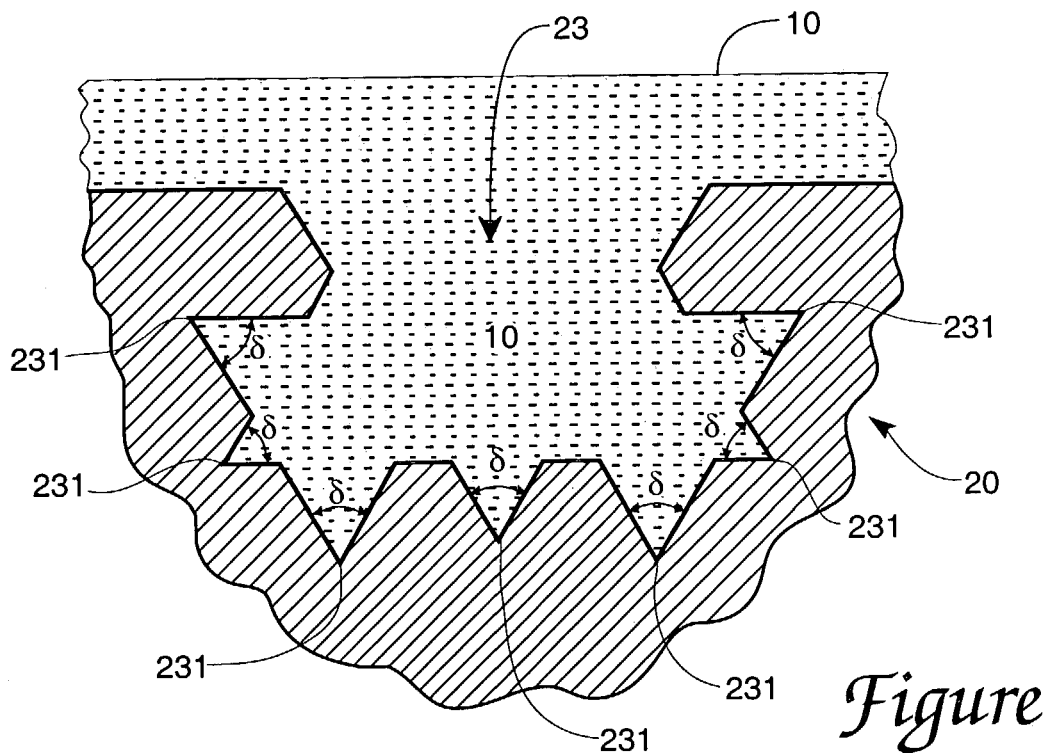
FIG. 7 shows a solid with a void having about 7 void included angles δ wherein the non-wetting liquid does reach the void vertices.

FIG. 7 shows a solid 20 with a void 23 having about 7 void included angles δ, which may be the same or different dimensions. In FIG. 7, the included angles δ are greater than the transitional included angle $\phi_t$ and complete contact between the non-wetting liquid 10 and the void vertex 231 occurs. Clearly, such perfect fractal geometry does not need to be in place. All that needs to exist are corners with included angles greater than the transitional included angle $\phi_t$ for complete contact with the void surface. It should be noted that although FIGS. 2a, 2b, 6, and 7 are drawn in two-dimension for convenience, the voids can be either two dimensional or 3-dimensional. That is, for example, the voids represented by these FIGS. can be formed by the intersection of plates, may be conical in shape, or possess another 3-dimensional shape.

The change in wetting behavior as a function of geometry can occur on a variety of scales from the macro-scale to the nano-scale. In addition, this selective alteration of the wetting behavior of a liquid on a particular surface can occur in a number of different ways. For example, one can modify the wetting behavior of a liquid on a surface by the arrangement of discrete pieces of material such as plates, by controlling the cross-sectional shape of a capillary or pore, or by modifying the surface topology by patterning or shaping of the surface on any scale. This patterning or shaping of the surface can involve a portion of the surface or the entire surface, can be regular or irregular, can involve depressions or elevations, and can be accomplished by a variety of means, such as mechanical means, energetic beams, physical or chemical processes, as well as a combination of these such as in photo-lithography. This may enable a wettability change on the surface of the solid without changing the chemical character or surface energy of the solid.

Capillaries with Non-Circular Cross-Sections

If a liquid wets a solid material, it will spontaneously flow into a capillary formed by that solid material. Likewise, a non-wetting liquid will not spontaneously flow into a capillary, and will only do so if pressure is applied. However, this traditional viewpoint assumes the diameter of the capillaries involved remains constant (linear) and/or the capillary is round (circular). If the diameters do not remain constant but vary in axial dimensions (commonly known as taper) and/or if the wall is composed of non-circular shapes, flow into or exclusion from a capillary, or a portion of the capillary cross-section, may or may not take place depending on the included angle formed by the walls of the capillary (capillary included angle δ'). This capillary included angle δ' can have any orientation with respect to the capillary principle axis. Thus, traditional viewpoints of whether or not a liquid will enter a capillary spontaneously need to be modified to include the very important effect of geometry.

Figure 8A:
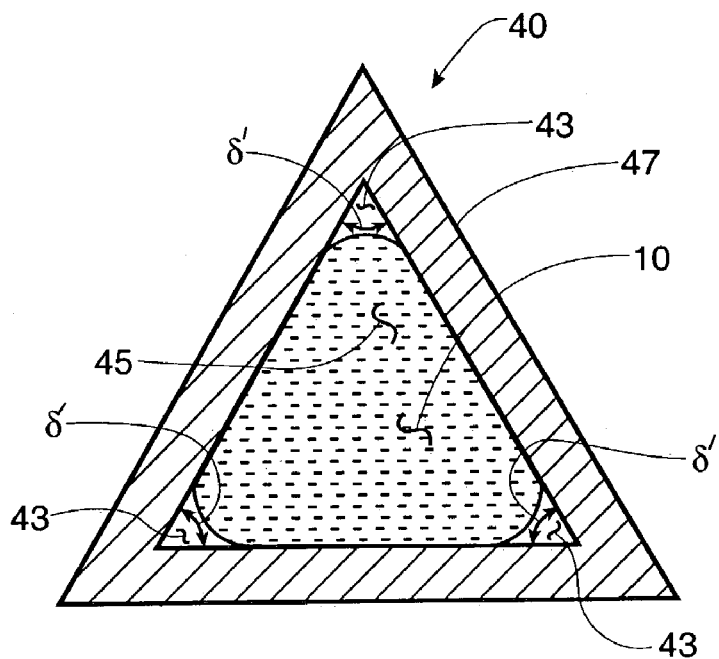
FIG. 8a shows a triangular capillary cross sectional geometry embodiment.
Figure 8B:
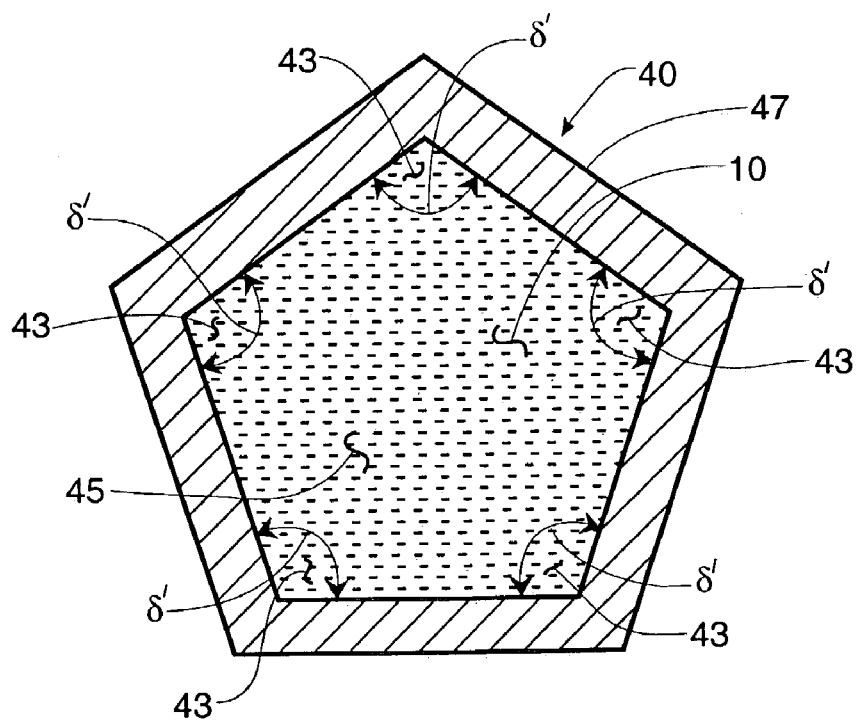
FIG. 8b shows a pentagon capillary cross sectional geometry embodiment.

The surface geometry of a solid may comprise a plurality of capillaries or the capillaries may be free-standing i.e.

single discrete capillary tubes. Each capillary has a cross-sectional geometry. FIG. 8a and FIG. 8b show two capillary cross-sectional geometry embodiments formed by the capillary wall 47. The capillary walls are shown with a uniform wall thickness for convenience. The wall thickness is immaterial to the invention so long as the fluid present does not distort the capillary dimensions. FIG. 8a shows a capillary 40, a non-wetting liquid 10 within the capillary 40 and a capillary path 45. In FIG. 8a, the non-wetting liquid 10 does not fill the capillary path 45 in a capillary vertex 43 region of the capillary included angles δ'.

FIG. 8b shows a capillary 40, a non-wetting liquid 10 within the capillary 40 and a capillary path 45. In FIG. 8b, the non-wetting liquid 10 fills the capillary path 45 in the vertex 43 region of the capillary included angles δ'. It is assumed, of course, that the contact angle θ is of such a value that this behavior would take place. If the contact angles θ were close enough to 90 degrees, even the three-walled polygon of FIG. 8a would be completely filled.

In addition to producing a desired interior capillary cross-section by shaping the capillary wall itself as seen in FIG. 8a and FIG. 8b, it is also possible to produce the desired included angles δ' in the interior capillary surfaces from depressions or protrusions in the capillary walls 47 themselves or by employing an insert into the capillary.

FIG. 8c and FIG. 8d show two capillary 40 cross-sectional geometry embodiments formed by an insert 49 placed inside the capillary wall 47. FIG. 8c and FIG. 8d illustrate flow of a non-wetting liquid in the capillary path 45 having multiple angled portions. FIG. 8c shows the capillary 40 with the path 45. The capillary path 45 includes 8 capillary included angles δ' and 8 capillary vertex regions 43. The liquid 10 is within the capillary path 45 but does not fill the capillary path 45 in the vertex 43 region of the capillary included angles δ'.

FIG. 8d shows a capillary 40 having a capillary path 45. The capillary path 45 includes 8 capillary included angles δ' and 8 capillary vertex regions 43. The liquid 10 is within the capillary path 45 and does fill the capillary path 45 in the vertex 43 region of the capillary included angles δ'. The liquid 10 fills the capillary path 45 in the vertex 43 of the capillary included angles δ' because the included angle δ' is greater than the transitional included angle $\phi_t$.

Capillary Device

The flow restrictions of various liquids near the vortex of the capillary may be used to create a capillary device 50 as shown in FIG. 9 in cross-section. The capillary device 50 includes a capillary device path 55 that may carry different immiscible non-wetting liquids in separate streams through different regions of the same capillary device path 55. Alternatively, the capillary device path 55 may carry a gas in combination with one or more immiscible non-wetting liquids in one or more separate streams through different regions of the same capillary device path 55. The capillary device 50 may include at least one angular portion 53 with a capillary included angle 531 and at least one open portion 54. The capillary open portion 54 may be curved as shown in FIG. 9 or include a capillary included angle δ' greater than the transitional included angle $\phi_t$ of the liquid/solid combination. Either would allow the liquid to flow in the open portion 54.

Such a capillary design could have several uses. For example, two non-wetting liquids with different contact angles θ and thus different transitional included angles $\phi_t$ may be kept separate in the same capillary device 50 using geometric means as shown in FIG. 9. A first liquid 11 with a first transitional included angle $\phi_{mw1}$ and a second liquid 22 with a second transitional included angle $\phi_{mw2}$ may flow separately in the same capillary channel 55. The second transitional included angle $\phi_{mw2}$ would be designed to be greater than the first transitional included angle $\phi_{mw1}$ such that only the first liquid 11 would flow in angular portion 53 in the space near the capillary included angle 531 and vertex 51. In one embodiment, the angular portion 53 is designed to have an angle 531 less than the second transitional included angle $\phi_{mw2}$ and greater than the first transitional included angle $\phi_{mw1}$ so that only the first liquid will flow in the angular portion 53 of the capillary. This geometric dependence of flow into or within a capillary device 50 can also be used to separate fluids in a mixture, for example, by allowing entrance to one or more liquids and denying access to the others. Alternatively, a liquid can occupy a portion of the capillary while a gas occupies the space near and in the capillary included angle 531 and vertex 51.

Liquids with Contact Angles <90°

Figure 10:
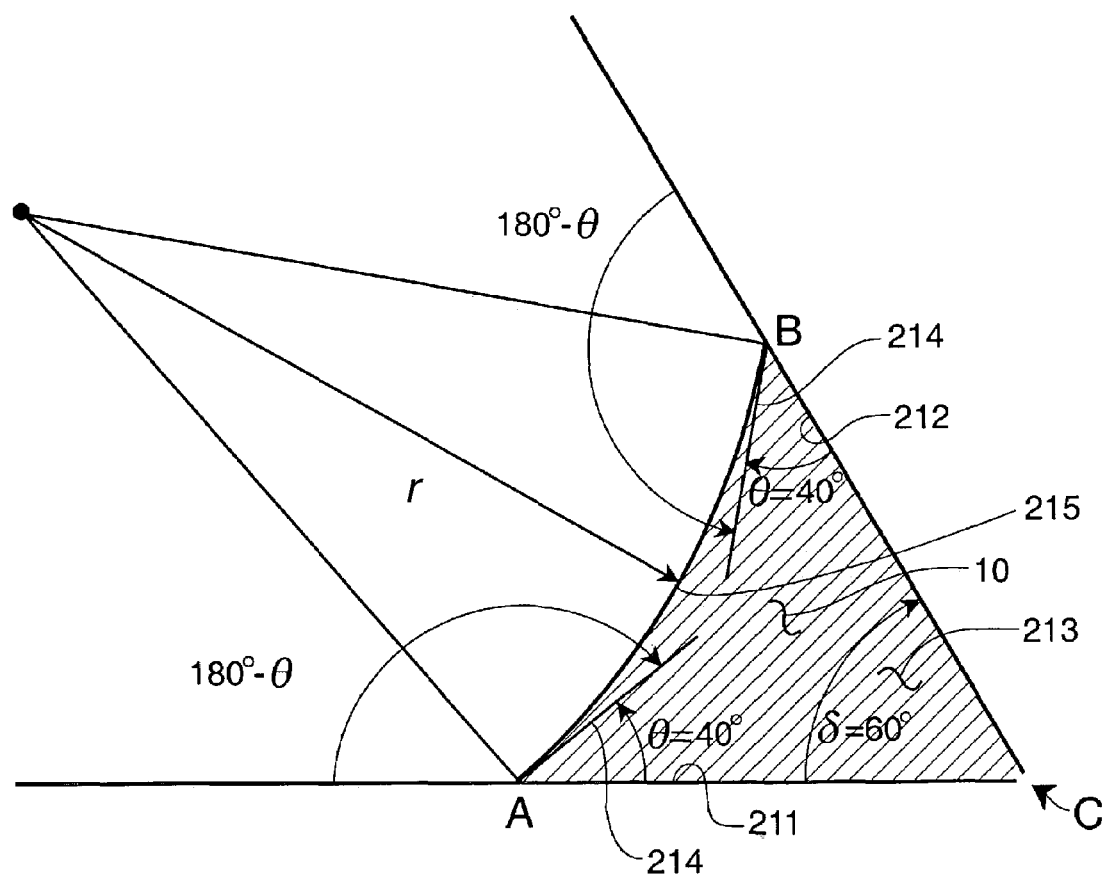
FIG. 10 shows a wetting liquid between a first solid surface and a second solid surface and the angular relationships with the contact angle θ.

FIG. 10 shows a wetting (contact angle θ<90°) liquid 10 between a first solid surface 211 and a second solid surface 212. The surfaces could be planar as shown or alternatively a sectional view of a cone, tapered capillary, or other 3-dimensional volume. This wetting liquid has a radius r and a contact angle θ with both solid surfaces of about 40 degrees. The contact angle θ is measured at point B on the second solid surface 212 and at point A on the first solid surface. The vertex of the two surfaces is at point C. It can be seen that the vertex (point C) is truncated to allow the entrance of the wetting liquid into an interstice 213. The angle formed by ACB, the actual angle formed by the solid surfaces, is called the included angle δ. In a manner similar to that shown for a non-wetting liquid in FIG. 3, whenever a wetting liquid has a contact angle, θ, with a solid surface that is less than 90 degrees, a relationship exists between an angle δ formed between two segments of that surface that determines whether or not liquid will enter the included angle through interstice 213. It should be noted that although the situation is similar between FIG. 3 and FIG. 10, there is a major difference. In FIG. 3, since the liquid is non-wetting it will not flow into the apex on its own accord, and will only enter if the included angle is greater than the transitional angle. In FIG. 10, the wetting liquid may enter vertex C on its own accord regardless of included angle δ if a significant quantity of liquid 10 was placed on either the first solid surface 211 or the second solid surface 212. The wetting liquid may also enter the vertex C on its own accord if the vertex C is lower than both surfaces. Thus, in FIG. 10, the liquid 10 is placed on the outside of the first solid surface 211 or the second solid surface 212 and only enters the interstice 213 if the included angle δ is less than the transitional included angle.

The transitional included angle for a wetting liquid, $\phi_{tw}$, is the included angle δ at which the tangents 214 to the droplet surface 215 originating at points A and B form a straight line. In the FIG. 10 example this would occur by increasing the included angle δ between the first solid surface 211 and the second solid surface 212. This transitional included angle $\phi_t$ may be used to differentiate between filling and non-filling behavior of the vertex C formed between the first solid surface 211 and the second solid surface 212. An algebraic analysis of the sides and angles of FIG. 10 provides the following equation for a wetting liquid.

In this case, the transitional included angle $\phi_{tw}$ is:

$$\phi_{tw} = 180° - 2\theta \quad (\theta \leq 90°) \qquad (3)$$

The contact angle θ is the angle that the liquid 10 makes with the solid surfaces 212/211. Both of which may be flat or curved solid surfaces.

As in the case of non-wetting liquids, equation 3 can be re-arranged so that the contact angle θ between a wetting liquid and a surface may easily be determined by measuring the transitional included angle $\phi_{tw}$. Rearranging equation 3 gives:

$$\theta = (180° - \phi_t)/2 \quad (\theta \leq 90°) \quad (4)$$

A similar phenomena to equation 1 for non-wetting liquids applies to "wetting liquids" having a contact angle θ with a solid surface that is between 0 degrees and 90 degrees. In exactly the same manner, it is easily demonstrated, both theoretically and experimentally, that a wetting liquid will only enter a capillary, pore, or corner from the smaller end, if the included angle δ is less than the transitional included angle ($\phi_{tw}$) given in equation 3.

Thus, it is not the relationship between the included angle and the contact angle that determines increased or decreased contact. It is the relationship between the included angle and the transition included angle. For wetting fluids, increased contact occurs if the included angle is less than the transitional included angle and for non-wetting fluids, increased contact occur if the included angle is greater than the transitional included angle.

Figure 11:
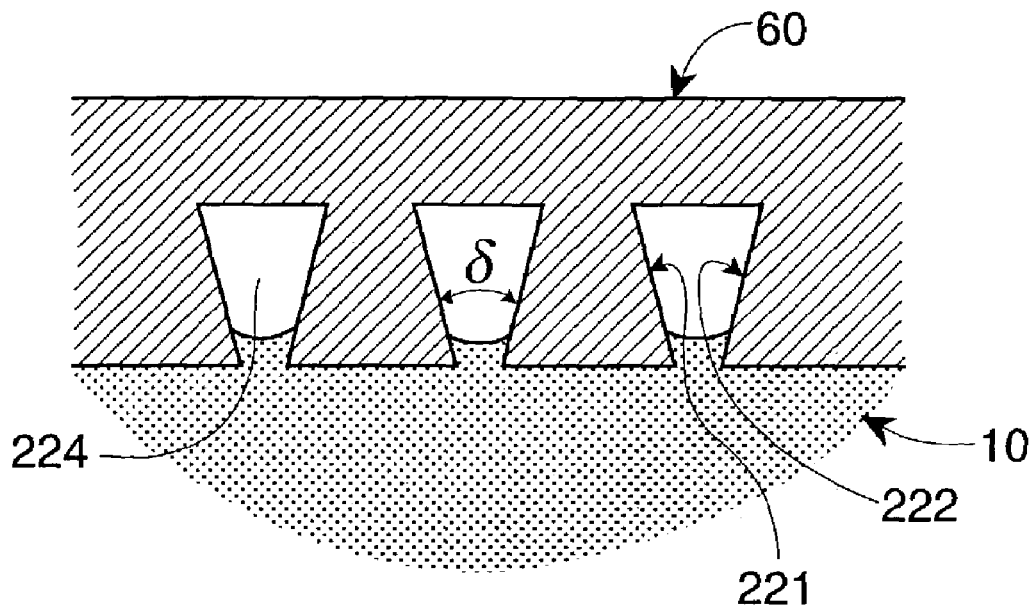
FIG. 11 shows a capillary cross sectional geometry embodiment with a wetting liquid.
Figure 12:
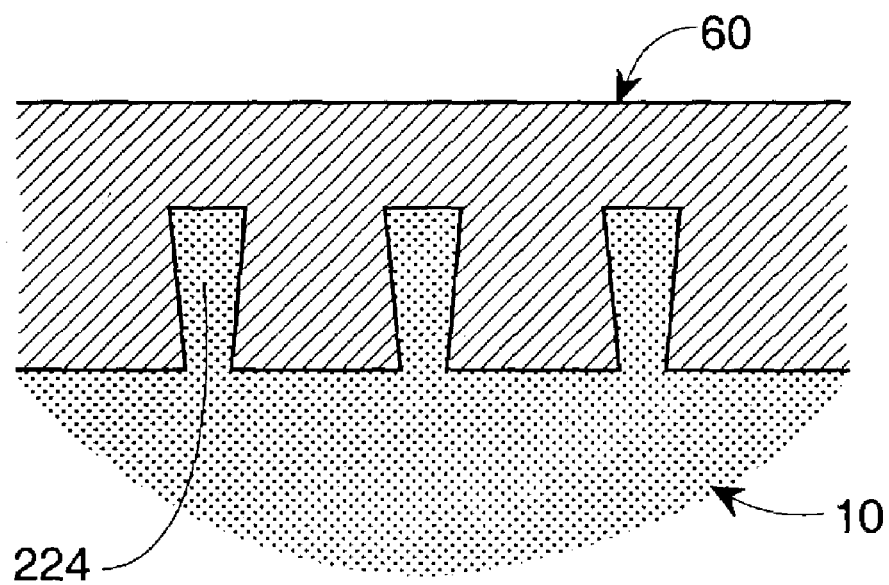
FIG. 12 shows a capillary cross sectional geometry embodiment with a wetting liquid.

This behavior can be seen in FIGS. 11 and 12 in which a three-dimensional plate 60 contains divergent sidewalls 221 and 222 respectively in one face of the plate. Sidewall 221 and sidewall 222 form an included angle δ and a void space 224. These divergent side walls 221 and 222 may be used to represent pores, capillaries, trenches, etc. that have expanding internal dimensions as they extend into the solid.

In one experiment the plates in FIG. 11 and FIG. 12 are fabricated from PLEXIGLAS® and the liquid is distilled water. Since distilled water on PLEXIGLAS® has a contact angle of about 75°, equation 3 predicts a transitional included angle of 30°.

In FIG. 11, the included angle δ is greater than the transitional included angle of 30° for water on PLEXIGLAS®, so water will not enter into the expanding vertices. However, in FIG. 12, the included angle δ is less than the transitional included angle, and complete filling of the void 224 takes place. These data indicate that three-dimensional pores having a taper angle may exhibit similar behavior.

Capillaries with Axial Variable Geometry

Figure 13:
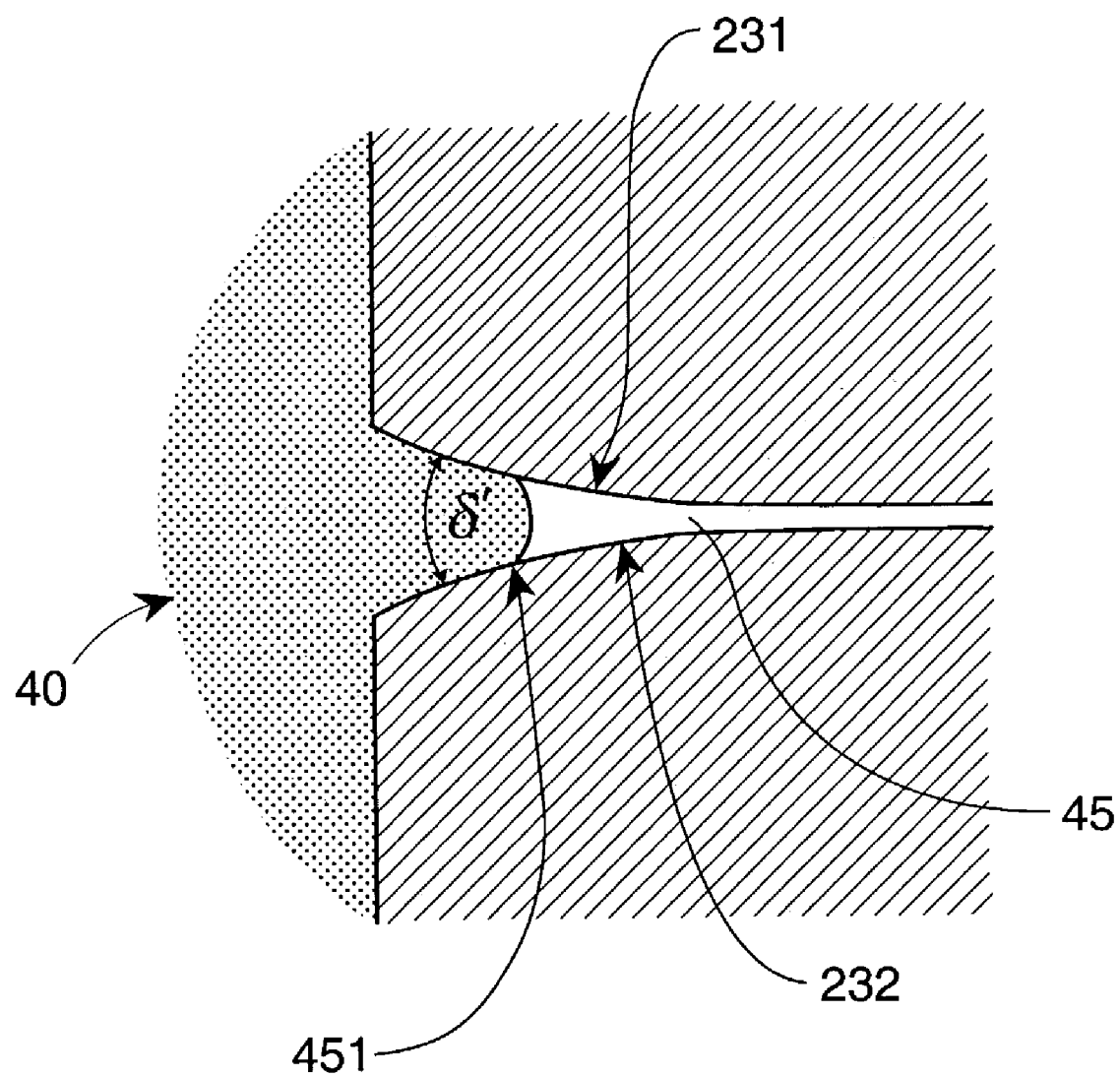
FIG. 13 shows a tapered capillary cross-section.

In some embodiments, the capillary cross sectional geometry may vary along a length of the capillary channel as in FIG. 13. FIG. 13 shows a side view of a round capillary 40 with a variable axial geometry. The capillary 40 has a tapered capillary path 45. The taper varies along the capillary path 45. The included angle δ' between the opposing capillary sides 231 and 232 may be orthogonal to the included angles δ' in FIGS. 8*a* and 8*b* although it need not be. In this example, the non-wetting liquid 10 will enter the capillary 40 until it reaches a point 451 in the capillary path 45 when the transitional included angle $\phi_{tw}$ for the particular liquid-solid material is reached. Although not shown, the capillary can also have a constant taper. In this instance, a non-wetting liquid with either enter the capillary or be denied access on the basis of the parameters in equation 1. In addition, the tapered capillaries can possess other cross-sectional shapes.

Other embodiments with tapered capillaries can be employed with wetting liquids. That is, tapered capillaries with the smaller end exposed to a wetting liquid can be used to allow or deny access of the wetting liquid into the capillary. It should be noted that these tapered capillaries like other capillaries in this application can be joined together to produce multi-function capillaries. For example, 1*a* tapered capillary can be joined at its smaller end to a linear capillary having the same diameter as the smaller end. This linear capillary can then be exposed to a wetting fluid. Now, if the taper is greater than the transitional included angle fluid penetration will stop at the beginning of the taper.

Dissimilar Surfaces

The opposing surfaces forming the included angle δ may be made of different materials and have different contact angles with the liquid. If the contact angles are not equal, but relatively similar, symmetry of the shape of the drop within the wedge-shaped included angle may be altered. The drop may contact the plate with the larger contact angle at a point closer to the vertex, and the transitional included angle $\phi_t$ may also be altered. In the extreme case of one plate being completely wetted by the liquid (contact angle of zero) and the other plate having a very large contact angle (approaching 180 degrees), the drop will spread out over the zero-contact-angle plate as much as possible, and attempt to not contact the other plate at all. This could be useful in applications where different material properties, such as emissivity or color, are desired to be observed when viewing the overall surface from different angles.

Wicking Behavior

In certain applications, such as heat pipe and spacecraft fuel tanks during zero gravity conditions, it is necessary for the liquid to spontaneously move from one location to another on the overall surface entirely because of capillary forces. This migrating behavior is commonly referred to as "wicking", and only occurs on planar surfaces if the contact angle approaches zero. If, however, the overall surface is covered with inverted V-shaped features, for example, that have an included angle δ less then the transitional included angle $\phi_{tw}$, the wetting liquid will increase both its contact with the surface and the volume of liquid being wicked considerably enhancing the wicking action. This is because the actual area of contact between the liquid and the solid surface has been increased. On the contrary, if the included angle δ is greater than the transitional included angle $\phi_{tw}$, some decrease in wicking activity in comparison to the flat surface will occur. By varying the included angle, it is possible to control the location on the overall surface to which the liquid will migrate.

Variable Area of Solid-Liquid Contact

In the preceding examples the solid-liquid contact angle θ between the liquid and the solid has been assumed constant, which means that the transitional included angle, $\phi_t$, calculated from either equation 1 or equation 3 is also constant. It is possible to change the solid-liquid contact angle θ by changing either the properties of the liquid and/or of the solid surface. This may be accomplished in any number of ways. For example, the temperature of the liquid can be changed, an electric field can be applied to the liquid, or the character of the liquid can be changed, for example, by combining with another liquid. In addition, the character of the surface can be modified by employing a heat-sensitive or light-sensitive coating, for example.

By purposeful selection of the material and surface characteristics of solids and the contacting liquids the degree of solid-liquid contact can be controlled. Through proper selection of the contact angle θ and included angle δ, the transitional included angle $\phi_t$ for the system can be fixed at a value close to that of the included angle δ of the surface features. In this case, a slight change in the liquid solid contact angle θ caused by changes in the liquid surface tension or by changes in the character of the surface will increase or decrease the area of contact between the liquid and the surface. Thus, the degree of wetting of the surface can be controlled by parameters, such as, temperature, radiation, and electromagnetic fields.

While the apparatus and method herein described constitute a preferred embodiment of the invention, it is to be understood that the invention is not limited to this precise form of apparatus or method and that changes may be made therein without departing from the scope of the invention which is defined in the appended claims.

We claim:

1. A transition included angle based method of predicting and controlling the wetting of a solid by a liquid comprising the steps of:
    providing a solid having a surface geometry,
    providing a liquid,
    placing the liquid in contact with the solid,
    measuring a transitional included angle formed between the solid and the liquid; and
    specifying the surface geometry of the solid at least in part based upon the transitional included angle to achieve a desired degree of wetting of the solid by the liquid.

2. The method of claim 1 wherein
    the surface geometry comprises a plurality of surface discontinuities, each surface discontinuity having at least one included angle;
    the liquid having a contact angle greater than about 90 degrees; and
    specifying the degree of wetting by sizing a plurality of the included angles be greater than or less than the transitional included angle.

3. The method of claim 1 wherein
    the surface geometry comprises a plurality of surface discontinuities, each surface discontinuity having at least one included angle with a truncated vertex with an opening;
    the liquid having a contact angle less than 90 degrees, impinging upon the truncated vertex, and able to enter the included angle only through the truncated vertex opening; and
    specifying the degree of wetting of the solid by controlling a plurality of the included angles with respect to the transitional included angle.

4. The method of claim 1 wherein the surface geometry comprises one or more tapered capillaries;
    each tapered capillary having at least one cross-sectional geometry and at least one axial geometry,
    the axial geometry having at least one capillary included angle resulting in a smaller end and a larger end;
    the liquid contacting the capillary smaller end, having a contact angle less than about 90 degrees with the solid; and
    wherein the degree of wetting of the solid may be controlled by specifying the size of a majority of the tapered capillary included angles with respect to the transitional included angle.

5. The method of claim 1 wherein the surface geometry comprises one or more capillaries, each capillary having at least one cross-sectional geometry and at least one axial geometry,
    the cross-sectional geometry or the axial geometry having at least one capillary included angle;
    the liquid having a contact angle greater than about 90 degrees with the solid; and specifying the degree of wetting of the solid by controlling a majority of the capillary included angles with respect to the transitional included angle.

6. The method of claim 1 wherein the surface geometry comprises one or more capillaries, each capillary having at least one cross-sectional geometry and at least one axial geometry,
    the cross-sectional geometry or the axial geometry having at least one capillary included angle;
    the liquid having a contact angle greater than about 90 degrees; and increasing the capillary flow of the liquid into the one or more capillaries by making a majority of the capillary included angles greater than the transitional included angle.

7. A capillary device with a capillary path for carrying at least a first fluid and a second fluid in separate streams, the capillary path having at least one capillary cross-section;
    the capillary cross-section including at least one first angular portion with a first capillary included angle with a vortex and at least one second portion;
    the first fluid is a gas or a liquid with a first contact angle and a first transitional included angle; the second fluid is a liquid that has a second contact angle greater than 90 degrees and a second transitional included angle greater than the first transitional included angle;
    the first angular portion having an included angle less than the second transitional included angle of the second fluid and greater than the first transitional included angle of the first fluid such that the first fluid flows nearer the vortex than the second portion and the second fluid flows nearer the second portion than the vortex.

8. The capillary device in claim 7 wherein the second portion is curved.

9. The capillary device in claim 7 wherein the first fluid is a liquid having
    a first contact angle greater than 90 degrees angle and a first transitional included angle greater than the included angle of the angular portion;
    the first fluid is immiscible with the second fluid.

10. A transition included angle based method of predicting and controlling the degree of contact between the surface of the capillary path of at least one capillary tube and a liquid comprising the steps of:
    providing a capillary tube having a cross-sectional shape and an axial shape;
    providing a liquid having a transitional included angle with the solid; and
    designing the cross-sectional shape or the axial shape of the capillary tube at least in part based upon the transitional included angle in order to achieve a desired capillary action between the tube and the liquid when the liquid and solid are placed in contact.

11. The method of claim 10 wherein the capillary flow of the liquid into the capillary is decreased by providing tapered capillaries with at least one cross-sectional geometry and at least one axial geometry, the axial geometry having at least one capillary included angle resulting in a smaller end and a larger end;
    the liquid having a contact angle less than about 90 degrees; and
    designing a majority of the capillary included angles to be greater than the transitional included angle in order to achieve a desired capillary action between the tube and the liquid when the liquid and capillary small end are placed in contact.

12. The method of claim 10 wherein the capillary flow of the liquid into the capillary is increased by providing capillaries with at least one cross-sectional geometry and at least one axial geometry, the cross-sectional geometry and the axial geometry having at least one capillary included angle;

the liquid having a contact angle greater than about 90 degrees in contact with the capillaries; and designing a majority of the capillary included angles to be greater than the transitional included angle to increase the capillary flow of the liquid into the capillary.

13. A method of analytically assessing a degree of contact between a solid with a plurality of surface included angles, at least one of which is a known surface included angle, and a liquid having a transitional included angle by comparing the transitional included angle with at least one known surface included angle.

14. A method of analytically assessing a liquid, having a transitional included angle, entering into a capillary having at least one known capillary included angle by comparing the transitional included angle with at least one known capillary included angle.

\* \* \* \* \*